United States Patent
Kim et al.

(10) Patent No.: US 11,345,661 B2
(45) Date of Patent: May 31, 2022

(54) METHOD FOR PURIFYING N-SUBSTITUTED MALEIMIDE

(71) Applicant: LG CHEM, LTD., Seoul (KR)

(72) Inventors: Eun Kyo Kim, Daejeon (KR); Jeong Seok Lee, Daejeon (KR); Mi Kyung Kim, Daejeon (KR); Joo Young Cheon, Daejeon (KR)

(73) Assignee: LG CHEM, LTD., Seoul (KR)

( * ) Notice: Subject to any disclaimer, the term of this patent is extended or adjusted under 35 U.S.C. 154(b) by 729 days.

(21) Appl. No.: 16/336,084

(22) PCT Filed: Jul. 9, 2018

(86) PCT No.: PCT/KR2018/007765
§ 371 (c)(1),
(2) Date: Mar. 22, 2019

(87) PCT Pub. No.: WO2019/132144
PCT Pub. Date: Jul. 4, 2019

(65) Prior Publication Data
US 2021/0355083 A1   Nov. 18, 2021

(30) Foreign Application Priority Data
Dec. 26, 2017 (KR) .......... 10-2017-0179166

(51) Int. Cl.
C07D 207/444 (2006.01)
C08F 222/40 (2006.01)
C08F 2/01 (2006.01)

(52) U.S. Cl.
CPC ........ *C07D 207/444* (2013.01); *C08F 2/01* (2013.01); *C08F 222/40* (2013.01)

(58) Field of Classification Search
CPC ....... C07D 207/444; C08F 2/01; C08F 222/40
See application file for complete search history.

(56) References Cited

U.S. PATENT DOCUMENTS

| | | | |
|---|---|---|---|
| 4,904,803 A * | 2/1990 | Fujita | C07D 207/452 548/549 |
| 5,136,052 A | 8/1992 | Van Gysel et al. | |
| 5,175,309 A | 12/1992 | Tsumura et al. | |
| 5,556,991 A | 9/1996 | Kita et al. | |
| 5,773,630 A | 6/1998 | Groth et al. | |

(Continued)

FOREIGN PATENT DOCUMENTS

| | | |
|---|---|---|
| CN | 2305235 Y | 1/1999 |
| CN | 102317260 A | 1/2012 |

(Continued)

OTHER PUBLICATIONS

Search Report dated Jun. 16, 2020 for European Application No. 18849469.4.

*Primary Examiner* — Robert D Harlan

(57) ABSTRACT

The present invention relates to a method for purifying N-substituted maleimide. More particularly, the present invention adopts an evaporation apparatus, which can previously remove impurities having higher boiling points than the N-substituted maleimide after removing an organic solvent from an N-substituted maleimide resulting solution, thereby achieving effects of minimizing the pressure loss and polymerization loss, and obtaining high-purity N-substituted maleimide.

19 Claims, 9 Drawing Sheets

(56) References Cited

U.S. PATENT DOCUMENTS

| | | | | |
|---|---|---|---|---|
| 5,993,687 A | * | 11/1999 | Kishino | ................ C07C 253/32 |
| | | | | 252/182.14 |
| 2003/0105337 A1 | | 6/2003 | Wu et al. | |
| 2011/0124882 A1 | | 5/2011 | Kim et al. | |
| 2020/0207710 A1 | * | 7/2020 | Cheon | ....................... C08F 8/30 |

FOREIGN PATENT DOCUMENTS

| | | |
|---|---|---|
| CN | 102850253 A | 1/2013 |
| EP | 0372922 A2 | 6/1990 |
| EP | 0627420 A1 | 12/1994 |
| JP | H01-216969 A | 8/1989 |
| JP | H05201972 A | 8/1993 |
| JP | H06135931 A | 5/1994 |
| JP | H07109258 A | 4/1995 |
| JP | 2003300956 A | 10/2003 |
| JP | 200622209 A | 1/2006 |
| KR | 1019910004790 B | 7/1991 |
| KR | 20090039133 A | 4/2009 |
| KR | 10-2015-0126872 A | 11/2015 |
| TW | 401387 B | 8/2000 |

\* cited by examiner

METHOD FOR PURIFYING N-SUBSTITUTED MALEIMIDE

CROSS-REFERENCE TO RELATED APPLICATIONS

This application is a U.S. National Stage of PCT/KR2018/007765, filed Jul. 9, 2018, which claims the benefit of Korean Patent Application Nos. 10-2017-0179166, filed on Dec. 26, 2017, in the Korean Intellectual Property Office, all of which is incorporated herein by reference.

TECHNICAL FIELD

The present invention relates to a method for purifying N-substituted maleimide.

BACKGROUND ART

An N-substituted maleimide compound is a useful compound as a raw material for a resin material, pharmaceutical and agricultural chemicals, etc., and particularly, widely used as one of copolymerization components for improving heat resistance of a styrene-based resin (for example, an ABS resin, an AS resin, an AB resin, an ACS resin, an AES resin, an AAS resin, etc.), a polyvinyl chloride resin, a poly methyl methacrylate resin, a phenol resin, etc. Among them, N-phenyl maleimide (hereinafter, also referred to as PMI) is particularly widely used because of having excellent reactivity and heat resistance.

As methods for preparing an N-substituted maleimide compound, there are many conventionally known methods, for example, 1) a method of obtaining an N-substituted maleimide compound by a dehydration reaction of maleic anhydride (hereinafter, also referred to as MAH) and a primary amine in one step, 2) a method of obtaining an N-substituted maleimide compound by a dehydration ring-closure imidization reaction of maleamic acid, which is produced from maleic anhydride and a primary amine, 3) a method of obtaining an N-substituted maleimide compound by a ring-closure imidization reaction of a corresponding maleamic acid monoester, etc.

Among these methods, the method 1) of obtaining an N-substituted maleimide compound from maleic anhydride and a primary amine in one step has a problem in that productivity is inferior because yield is still low; the method 3) of obtaining an N-substituted maleimide compound from a maleamic acid monoester has a problem in that an alcohol, which is produced by a ring-closure imidization reaction, is left and mixed in a product. Thus, the method 2) of obtaining an N-substituted maleimide compound by a dehydration ring-closure imidization reaction of a maleamic acid is commercially and generally carried out.

On the other hand, when N-phenyl maleimide is prepared, a primary amine is aniline (hereinafter, also referred to as ANL), and a maleamic acid is an N-phenyl maleamic acid (hereinafter, also referred to as PMA).

Reaction products produced by the reaction include unreacted maleic anhydride, a solvent for dissolving reactants, by-products resulting from the reaction, oligomers, a catalyst, etc. in addition to the N-substituted maleimide.

In order to separate/purify the N-substituted maleimide, a process such as washing with water, extracting, or distilling may be used, but the process of washing with water has environmental and economic problems because a lot of wastewater is produced. In addition, the extracting process has a problem in that high-purity purification is difficult because impurities as well as the N-substituted maleimide are highly likely to be extracted; and the distilling process has a problem in that purification loss occurs because polymerization of the N-substituted maleimide occurs in high-temperature distillation due to a high boiling point of the N-substituted maleimide.

Meanwhile, vacuum distillation may be carried out because the operating temperature of a distillation column needs to be lowered in order to minimize purification loss in the purification method through the distilling process, but there is a limitation in vacuum pressure available in a commercial distilling process. Particularly, in order to remove impurities having higher boiling points than the N-substituted maleimide through a distillation column, there is a problem in that the bottom temperature of the distillation column, that is, the operating temperature of a reboiler is increased, thereby increasing polymerization loss. Thus, this problem should be solved.

Accordingly, the present invention provides a purification method which can minimize purification loss without producing wastewater as an environmental problem.

PRIOR ART DOCUMENT (Patent Document 1) U.S. Pat. No. 5,136,052 A (1992 Aug. 4)

DISCLOSURE OF THE INVENTION

Technical Problem

An aspect of the present invention provides a method for purifying an N-substituted maleimide compound, the method being capable of minimizing purification loss (polymerization loss) without producing washing wastewater.

Another aspect of the present invention provides a method for purifying an N-substituted maleimide compound, the method being easy to operate and enabling a continuous operation to be performed commercially.

Technical Solution

To solve the above-described problems according to the aspects of the present invention, there is provided a purification method for N-substituted maleimide, including:

1) performing a primary purification by introducing an N-substituted maleimide solution into a first distillation column and removing an organic solvent by distilling; and 2) performing a secondary purification by introducing, into an evaporation apparatus, an N-substituted maleimide residue from which the organic solvent is removed, and removing impurities which have higher boiling points than the N-substituted maleimide.

Advantageous Effects

The method for purifying the N-substituted maleimide according to the present invention does not perform a water washing process, so that the method is eco-friendly without a water washing process, and does not require an additional wastewater treatment facility and costs for maintaining the same, thereby providing economic effects.

In addition, the method for purifying the N-substituted maleimide according to the present invention has an effect of obtaining high-purity N-substituted maleimide since an apparatus which can minimize pressure loss is additionally provided.

In addition, the purification method for the N-substituted maleimide according to the present invention has effects in which an operation is easy and a continuous operation can be performed commercially.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Figure 1:
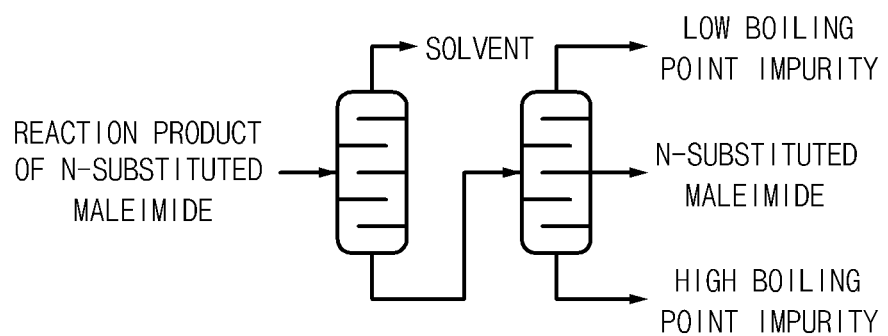
FIG. 1 is a schematic view illustrating a purification method for N-substituted maleimide according to Comparative Example (conventional method).

Hereinafter, the present invention will be described in more detail to allow for a clearer understanding of the present invention.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

The present invention provides a method for purifying N-substituted maleimide, including:

1) performing a primary purification by introducing an N-substituted maleimide solution into a first distillation column and removing an organic solvent by distilling; and 2) performing a secondary purification by introducing, into an evaporation apparatus, the N-substituted maleimide residue from which the organic solvent is removed, and removing impurities which have higher boiling points than the N-substituted maleimide.

Hereinafter, the method for purifying N-substituted maleimide of the present invention will be described in detail.

Step 1)

The step 1) according to one example of the present invention is primarily purifying an N-substituted maleimide solution produced by an N-substituted maleimide synthesis reaction, the step being characterized by introducing the N-substituted maleimide solution into the first distillation column and removing the organic solvent by distilling.

The N-substituted maleimide solution produced by the N-substituted maleimide synthesis includes not only the N-substituted maleimide but by-products such as an organic solvent, an unreacted maleic anhydride, and an organic acid, and impurities such as oligomers in which N-substituted maleimide is partially polymerized.

On the other hand, the organic acid impurity may include at least one selected from the group consisting of fumaric acid (FA), maleic acid (MA), maleic anhydride (MAH), N-phenyl maleamic acid (PMA), N-(2,5-dioxo-1-phenyl-3-pyrrolidinyl)-N-phenyl maleamic acid) (PPMA), N-(2,5-dioxo-1-phenyl-3-pyrrolidinyl)-N-phenylfumaramic acid) (PPFA) and 2-anilino-N-phenyl succinimide (APSI), and among them, the impurities having higher boiling points than the N-substituted maleimide may be at least one selected from the group consisting of N-(2,5-dioxo-1-phenyl-3-pyrrolidinyl)-N-phenyl maleamic acid) (PPMA), N-(2,5-dioxo-1-phenyl-3-pyrrolidinyl)-N-phenylfumaramic acid) (PPFA) and 2-anilino-N-phenyl succinimide (APSI).

In addition, the organic solvent removed in the primary purification may be at least one selected from the group consisting of benzene, toluene, xylene, o-xylene, ethylbenzene, isopropylbenzene, cumene, mesitylene, tert-butylbenzene, pseudocumene, trimethylhexane, octane, tetrachloroethane, nonane, chlorobenzene, ethylcyclohexane, m-dichlorobenzene, sec-butylbenzene, p-dichlorobenzene, decane, p-cymene, o-dichlorobenzene, butylbenzene, decahydronaphthalene, tetrahydronaphthalene, dodecane, naphthalene and cyclohexylbenzene.

In this way, the reason why the organic solvent contained in the N-substituted maleimide solution is distilled and removed previously in purification for the N-substituted maleimide is that the boiling point of the organic solvent is lower than that of another impurity and the boiling point difference from the other impurity is also large, so it is easy to distill and separate the organic solvent. Also, the reason why the organic solvent is distilled earlier than the high-boiling-point impurity is that the organic solvent is contained in a large amount in the N-substituted maleimide solution, so that the organic solvent is separated in advance to reduce a feed flow rate, thereby reducing a load exerted on a subsequent purification process.

In the primary purification, the first distillation column may be operated under pressure of 20 to 80 torr, more preferably 20 to 70 torr. Since further lowering the operating pressure of the first distillation column has a limitation in the apparatus system, there is a difficulty in performing a continuous operation commercially. When the pressure is higher than the above range, the operating temperature may be increased to cause difficulty in supplying utility or increasing of the utility cost, and cause the polymerization of the N-substituted maleimide, thereby leading to a problem of fouling or lowering the purification yield. Therefore, it is preferable to operate within the above range.

Under the above operating pressure of the first distillation column, the reboiler at the bottom of the first distillation column may be operated at a temperature from 170 to 220° C., more preferably 180 to 210° C. When the reboiler at the bottom of the first distillation column is operated within the above range, it is effective for removing the organic solvent while suppressing fouling caused by the polymerization of the N-substituted maleimide or factors that prevent stable and continuous operation due to increasing of the operating temperature, and thus there is an advantage in that the purification loss due to the polymerization of the N-substituted maleimide can be reduced.

On the other hand, in the primary purification, impurities having lower boiling points than the N-substituted maleimide may be further removed in addition to the organic solvent by changing the operating conditions for the first distillation column.

In this case, since the operating temperature of the reboiler at the bottom of the first distillation column becomes higher, there is a disadvantage in that the purification loss due to the polymerization of the N-substituted maleimide may partially occur compared to the case of removing only the organic solvent. However, when all of the low-boiling-point impurities are removed in the primary purification, there is no need to further remove the low-boiling-point impurities in subsequent processes, and thus there may be an advantage in that the purification process is simplified.

Step 2)

The step 2) according to one example of the present invention is secondarily purifying the N-substituted maleimide residue from which the organic solvent is removed in step 1), the step being characterized by introducing, into an evaporation apparatus the N-substituted maleimide residue from which the organic solvent is removed to thereby remove impurities having higher boiling points than the N-substituted maleimide.

The present invention provides the method for purifying the N-substituted maleimide for obtaining high-purity N-substituted maleimide, wherein distilling is used for the method, so that it is eco-friendly in that it does not generate washing wastewater, and it has an economic effect in that an additional wastewater treatment facility and cost for maintaining the same are unnecessary.

However, in order to remove the impurities having higher boiling points than the N-substituted maleimide compound through the distillation, the distillation should be carried out at high temperature, and there is a problem in that the polymerization of the N-substituted maleimide occurs at high temperature and the purification loss occurs. Thus, the low-pressure distillation is inevitable in order to lower the boiling points of the high-boiling-point impurities.

Even if the distillation column is operated through the low-pressure distillation, there is a limitation to increase the vacuum degree of the distillation column which can be operated continuously and commercially, and there is also a limitation to lower the operating temperature of the reboiler at the bottom of the distillation column due to pressure losses in upper and lower regions which are the characteristics of the distillation column.

Therefore, the conventional distilling purification methods, in which the operating temperature of the reboiler at the bottom of the distillation column is high and the residence time at the high temperature bottom of the distillation column is long, have a problem in that the purification loss, such as the polymerization loss, is increased.

Here, at each tray of the distillation column, while a liquid phase flows to the lower tray and a gas phase rises to the upper tray, the gas and liquid phases come into contact with each other and the phases are separated by phase equilibrium. In the process, the pressure loss occurs and the distillation column has a pressure difference between upper and lower regions in which the lower region is higher in pressure than the upper region of the distillation column. Accordingly, this phenomenon means the pressure loss. In addition, the polymerization loss means that the polymerization reaction between the N-substituted maleimide compounds partially occurs at the high temperature, and thus the N-substituted maleimide compound as the final product is partially lost. The higher the reboiler temperature at the bottom of the distillation column, the more the polymerization loss rate increases.

Accordingly, the present invention has solved the above conventional problem by introducing a secondary purification in which an evaporation apparatus capable of removing the impurities which have higher boiling points than the N-substituted maleimide was used.

When the secondary purification using the evaporation apparatus of the present invention is carried out, it is possible to remove the impurities having higher boiling points than the N-substituted maleimide at the lower temperature than that of the distillation column, and it is possible to minimize the residence time in which the N-substituted maleimide residue stays in the evaporation apparatus. Thus, the purification loss, such as the above polymerization loss, can be minimized by the secondary purification.

On the other hand, the impurities having higher boiling points than the N-substituted maleimide may be at least one selected from the group consisting of N-(2,5-dioxo-1-phenyl-3-pyrrolidinyl)-N-phenyl maleamic acid) (PPMA), N-(2,5-dioxo-1-phenyl-3-pyrrolidinyl)-N-phenylfumaramic acid (PPFA), and 2-anilino-N-phenyl succinimide (APSI).

The evaporation apparatus of the present invention may be at least one selected from the group consisting of a thin film evaporator, a falling film evaporator, and a flash drum.

In addition, the evaporation apparatus may be operated under pressure of 5 to 30 torr, preferably 5 to 20 torr, more preferably 5 to 10 torr. By using the evaporation apparatus characterized by the high vacuum in the above range, the present invention enables continuous operation to be performed commercially, and can easily remove impurities having higher boiling points than the N-substituted maleimide.

In addition, the evaporation apparatus may be operated at a temperature from 100 to 180° C., preferably 120 to 150° C. By operating at the temperature in the above range, the present invention can evaporate and remove the impurities having higher boiling points than the N-substituted maleimide at a low temperature in comparison with the distillation column, and thus there is an effect of reducing the polymerization loss between the N-substituted maleimide products.

Furthermore, the N-substituted maleimide residue in the evaporation apparatus may be resided for 20 seconds to 5 minutes, preferably 30 seconds to 2 minutes. The present invention has an advantage of maximizing a heat transfer surface area in the high-vacuum evaporation apparatus by evaporating impurities, which have higher boiling points than the N-substituted maleimide, as desired while reducing the residence time, and in this case, there is an advantage in that the polymerization loss can be reduced by shortening an exposure time to a high temperature.

However, the evaporation apparatus has a disadvantage in that the separation efficiency is not excellent in comparison with the distillation column. Specifically, in the secondary purification using the evaporation apparatus of the present invention, the impurity having a large difference in a boiling point from the N-substituted maleimide is easily separated, but the separation efficiency of the impurity having a small difference in a boiling point from the N-substituted maleimide is not excellent. Thus when there is a substance having a small difference in a boiling point from the N-substituted maleimide in the impurity, it is advantageous to purify into high-purity N-substituted maleimide by carrying out an additional purification process using a distillation column capable of removing such the impurity.

Accordingly, the method for purifying the N-substituted maleimide of the present invention is characterized by using an evaporation apparatus for removing impurities having higher boiling points than the N-substituted maleimide and a distillation column having the excellent separation efficiency together.

In the secondary purification, the residue including impurities which have higher boiling points than the N-substituted maleimide may be discharged through the lower portion of the evaporation apparatus.

Step 3)

The step 3) according to one example of the present invention is performing tertiary purification of the N-substituted maleimide distillate passed through the secondary purification of the step 2), the step being characterized by introducing the N-substituted maleimide distillate from which the impurities having higher boiling points than the N-substituted maleimide are removed into a second distillation column and by distilling.

The second distillation column in the tertiary purification may be operated under pressure of 20 to 80 torr, preferably 20 to 70 torr.

In the secondary purification, the evaporation apparatus is introduced to previously remove the high-boiling-point impurity having a large difference in a boiling point from the N-substituted maleimide, thereby lowering the temperature at the bottom of the second distillation column in the tertiary purification and decreasing the polymerization. As a result, an increasing effect of the purification yield according to the decreasing of the purification loss can be obtained. Also, there is a study that the high-boiling-point impurity promotes the N-substituted maleimide polymerization, and thus, by previously removing a part of the high-boiling-point impurities, a double effect of the decreasing polymerization can be obtained through the second distillation column in the tertiary purification. The distillation column of the tertiary purification is capable of purifying into the high-purity N-substituted maleimide, so that there is an effect of increasing the purity of the N-substituted maleimide while operating continuously and commercially.

In addition, under the above operating pressure of the second distillation column, the reboiler at the bottom of the second distillation column in the tertiary purification may be operated at a temperature from 190 to 230° C., preferably 190 to 220° C. When the operating temperature of the reboiler at the bottom of the second distillation column is within the above range, it is effective to remove the impurities while suppressing the occurrence of the N-substituted maleimide polymerization, and thus there is an advantage in that the purification loss by the N-substituted maleimide polymerization can be reduced.

On the other hand, the second distillation column in the tertiary purification may have slightly higher in operating temperature than the first distillation column in the primary purification, and this is because the concentration of the high-boiling-point impurities is higher than that of a bottom flow composition of the first distillation column. However, since the process of removing part or all of the high-boiling-point impurities in the secondary purification is carried out, the bottom temperature may be lower or an amount of the bottom flow may become smaller than the case in which the secondary purification is not carried out.

The tertiary purification is an optional purification and may be thus omitted when all of the impurities, which have lower or higher boiling points than the N-substituted maleimide in the primary and secondary purification, are removed.

When all of the impurities, which have lower or higher boiling points than the N-substituted maleimide in the primary purification and secondary purification, are removed, or when the N-substituted maleimide distillate passed through the primary purification and secondary purification satisfies the desired purity standard, the high-purity N-substituted maleimide as the final product can be obtained from the distillate discharged through the lower portion of the evaporation apparatus in the secondary purification without carrying out the tertiary purification.

However, when all of the impurities, which have lower or higher boiling points than the N-substituted maleimide in the primary purification and secondary purification, are not removed, or when the N-substituted maleimide distillate passed through the primary purification and secondary purification does not satisfy the desired purity standard, the tertiary purification can be essentially performed in order to obtain the high-purity N-substituted maleimide.

More specifically, according to whether to remove the impurities, which have lower or higher boiling points than the N-substituted maleimide in the primary purification and secondary purification, that is, according to the N-substituted maleimide distillate composition that has experienced the secondary purification, the method for purifying the N-substituted maleimide can be carried out in four ways.

(First N-Substituted Maleimide Purification Method)

Figure 2:
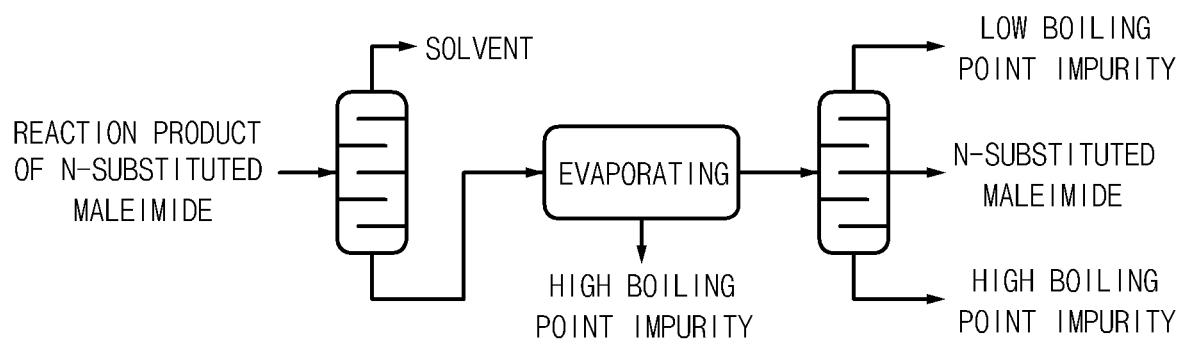
FIG. 2 is a schematic view illustrating a first purification method for N-substituted according to the present invention.

As illustrated in FIG. 2, when all of the low-boiling-point impurities are not removed in the primary purification and when all of the high-boiling-point impurities are not removed in the secondary purification, all the low-boiling-point and high-boiling-point impurities can be removed in the tertiary purification.

When the reboiler operating temperature at the bottom of the first distillation column is slightly lowered to suppress the N-substituted maleimide polymerization loss in the primary purification, all of the low-boiling-point impurities may not be removed in the primary purification. In this case, the N-substituted maleimide polymerization loss in the first distillation column may be suppressed, but all of the low-boiling-point impurities remaining in the second distillation column of the tertiary purification should be removed by distilling into the upper portion, and thus there may be a disadvantage in that the reboiler load at the bottom of the second distillation column increases slightly.

However, when the high-boiling-point impurities partially remain in the N-substituted maleimide distillate passed through the secondary purification, the remaining high-boiling-point impurities should be removed in the tertiary purification. In this case, the reboiler operating temperature at the bottom of the second distillation column in the tertiary purification may be slightly increased in comparison with the case of not containing the high-boiling-point impurities in the N-substituted maleimide distillate, but there is an advantage in that the operating temperature is low in comparison with the conventional case of not using the evaporation apparatus in the secondary purification.

(Second N-Substituted Maleimide Purification Method)

Figure 3:
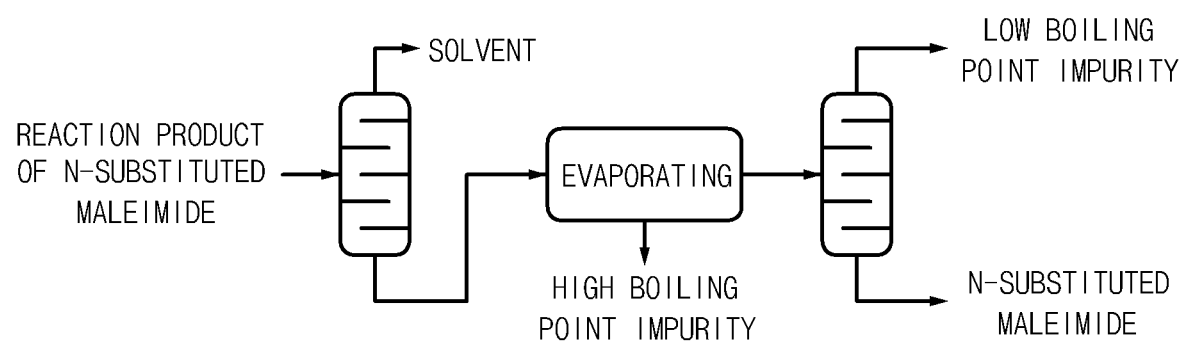
FIG. 3 is a schematic view illustrating a second purification method for N-substituted maleimide according to the present invention.

As illustrated in FIG. 3, when all of the low-boiling-point impurities are not removed in the primary purification and all of the high-boiling-point impurities are removed in the secondary purification, the low-boiling-point impurities can be removed in the tertiary purification.

When the reboiler operating temperature at the bottom of the first distillation column is slightly lowered to suppress the N-substituted maleimide polymerization loss in the primary purification, all of the low-boiling-point impurities may not be removed in the primary purification. In this case, the N-substituted maleimide polymerization loss in the first distillation column may be suppressed, but all of the low-boiling-point impurities remaining in the second distillation column of the tertiary purification should be removed by distilling into the upper portion, and thus there may be a disadvantage in that the reboiler load at the bottom of the second distillation column increases slightly.

However, all of the high-boiling-point impurities are removed in the second purification, and only the low-boiling-point impurities and the N-substituted maleimide are left in the N-substituted maleimide distillate passed through the secondary purification, and thus the N-substituted maleimide, which is the final product, can be obtained at the bottom of the second distillation column, not as a distillate but as a residue. In this case, since it is necessary to distill only the low-boiling-point impurities without distilling all of the N-substituted maleimide, the reboiler operating temperature at the bottom of the second distillation column in the tertiary purification can be greatly lowered. Also, since an amount of distilling through the reboiler is small, the residence time of staying in the second distillation column can be shortened. As a result, the N-substituted maleimide polymerization loss can be effectively suppressed.

(Third N-Substituted Maleimide Purification Method)

Figure 4:
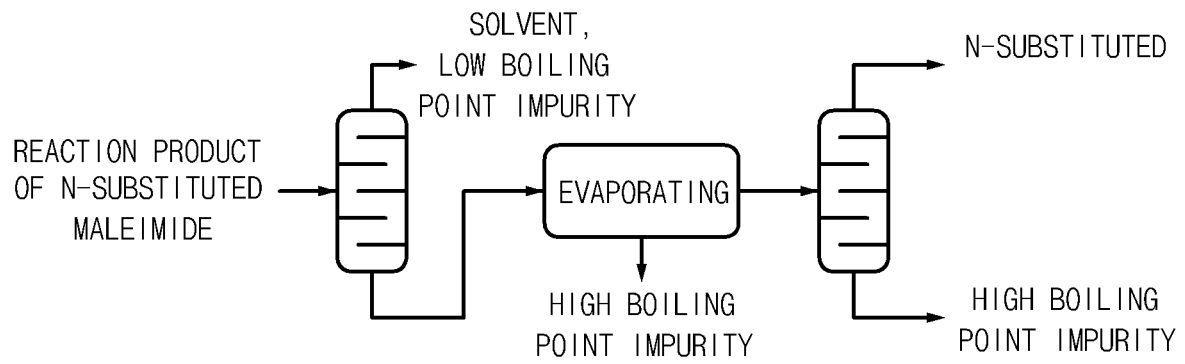
FIG. 4 is a schematic view illustrating a third purification method for N-substituted maleimide according to the present invention.

As illustrated in FIG. 4, when all of the low-boiling-point impurities are removed in the primary purification and all of the high-boiling-point impurities are not removed in the secondary purification, the high-boiling-point impurities can be removed in the tertiary purification.

In the primary purification, when the reboiler operating temperature at the bottom of the first distillation column is slightly raised in order to remove all of the low-boiling-point impurities, there may be an advantage in that it is unnecessary to additionally remove the low-boiling-point impurities in the tertiary purification while the N-substituted maleimide polymerization loss may partially occur in the first distillation column.

However, when the high-boiling-point impurities partially remain in the N-substituted maleimide distillate passed through the secondary purification, the remaining high-boiling-point impurities should be removed in the tertiary purification. In this case, the reboiler operating temperature at the bottom of the second distillation column in the tertiary purification may be slightly high in comparison with the case of not containing the high-boiling-point impurities in the N-substituted maleimide distillate, but there is an advantage in that the operating temperature is low in comparison with the conventional case of not using the evaporation apparatus in the secondary purification.

(Fourth N-Substituted Maleimide Purification Method)

Figure 5:
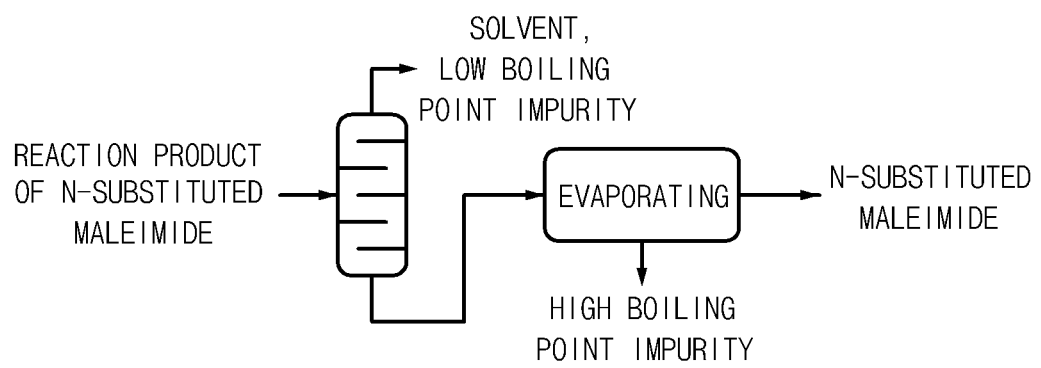
FIG. 5 is a schematic view illustrating a fourth purification method for N-substituted maleimide according to the present invention.

As illustrated in FIG. 5, when all of the low-boiling-point impurities are removed in the primary purification and all of the high-boiling-point impurities are removed in the secondary purification, the tertiary purification may be unnecessary.

In the primary purification, when the reboiler operating temperature at the bottom of the first distillation column is slightly raised in order to remove all of the low-boiling-point impurities, there may be an advantage in that it is unnecessary to additionally remove the low-boiling-point impurities in the tertiary purification while the N-substituted maleimide polymerization loss may partially occur in the first distillation column.

In addition, when the high-boiling-point impurities are not left in the N-substituted maleimide distillate that has been subjected to the secondary purification, the high-purity N-substituted maleimide as the final product can be obtained from the distillate discharged through the lower portion of the evaporation apparatus in the secondary purification without carrying out the tertiary purification, and thus there is an advantage of simplifying the process.

As described above, the N-substituted maleimide purification method of the present invention, in which the secondary purification using the evaporation apparatus is introduced in order to remove impurities having higher boiling points than the N-substituted maleimide, can minimize the polymerization loss due to the distillation, and thus the polymerization loss ratio may be 10% or less, preferably 5% or less at 190° C., and 30% or less, preferably 15% or less at 210° C.

In addition, since the N-substituted maleimide purification method of the present invention is capable of operating the distillation column at more relaxed conditions such as temperature and pressure conditions, a continuous purification of a large amount of the N-substituted maleimide is possible commercially, thereby increasing the productivity of the final product, and there is also an effect of obtaining the high-purity N-substituted maleimide having a purity of 95% or more, preferably 99% or more.

On the other hand, the N-substituted maleimide may include at least one selected from the group consisting of: N-alkyl maleimide such as N-methyl maleimide, N-ethyl maleimide, N-hexyl maleimide, N-octyl maleimide, or N-dodecyl maleimide; N-benzyl maleimide; N-cycloalkyl maleimide such as N-cyclohexyl maleimide; N-phenyl maleimide; or N-substituted phenyl maleimide, in which a phenyl group is substituted with a nitro group, an alkoxy group, an alkyl group, a carboxyl group, a hydroxyl group, or a halogen group, such as N-nitrophenyl maleimide, N-methoxyphenyl maleimide, N-methylphenyl maleimide, N-carboxyphenyl maleimide, N-hydroxyphenyl maleimide, N-chlorophenyl maleimide, N-dimethylphenyl maleimide, N-dichlorophenyl maleimide, N-bromophenyl maleimide, N-dibromophenyl maleimide, N-trichlorophenyl maleimide, or N-tribromophenyl maleimide.

Example 1

An N-phenyl maleimide solution, from which a catalyst is separated and which is composed of 66.7 wt. % of ethylbenzen, 0.54 wt. % of maleic anhydride, 0.09 wt. % of FA, 0.57 wt. % of PMA, 25.84 wt. % of PMI, 0.34 wt. % of PPMA, 0.15 wt. % of APSI, and 5.48 wt. % of unmeasured quantity (others), was introduced into a first distillation column and the ethylbenzene was removed through a primary purification operated under a pressure of 30 torr and at a reboiler temperature of 190° C. Then, the resultant solution was introduced into a thin film evaporator and a secondary purification was completed by operating the thin film evaporator under a pressure of 5 torr and at a temperature of 140° C. for 1 hour. Thereafter, the N-phenylmaleimide distillate that had been subjected to the secondary purification was introduced into a second distillation column and a tertiary purification was completed by operating the second distillation column under a pressure of 20 torr and at a temperature of 190° C. for 1 hour.

Example 2

The N-phenyl maleimide was purified in the same manner as in Example 1 except that the second distillation column in Example 1 was operated under 60 torr and at 210° C. for 1 hour.

Example 3

The N-phenyl maleimide was purified in the same manner as in Example 1 except that all of the low-boiling-point impurities were removed at a higher temperature than that in Example 1 by allowing the first distillation column in Example 1 to be operated under an operating pressure of 30 torr and at a reboiler operating temperature in the bottom of the first distillation column of 200° C., thereby not carrying out the tertiary purification.

Comparative Example 1

The N-phenyl maleimide was purified in the same manner as in Example 1 except that after separating ethylbenzene through the primary purification in Example 1, the N-phenyl maleimide residue, which was collected from the bottom of the first distillation column in the primary purification, was directly introduced into the second distillation column in the tertiary purification without the secondary purification, and the residue was purified by operating the second distillation column under a pressure of 20 torr and at a temperature of 190° C. for 1 hour.

Comparative Example 2

The N-phenyl maleimide was purified in the same manner as in Comparative Example 1 except that the second distillation column of the tertiary purification in Comparative Example 1 was operated under a pressure of 60 torr and at a temperature of 210° C. for 1 hour.

Experimental Examples

In comparison with the above Examples and Comparative Examples, the following experiments were carried out to directly or indirectly show the purifying effects of the N-phenyl maleimide, and the results were shown below.

1) Confirming the removal effect of the high-boiling-point impurities from the thin film evaporator (Examples 1 and 3)

In order to confirm that impurities having higher boiling points than the N-substituted maleimide were removed in the secondary purification of Example 1, the composition of the N-substituted maleimide feed which has passed through the primary purification and then was introduced into the thin film evaporator, and the distillate and residue in the thin film evaporator were measured by using liquid chromatography, and the results were shown in below Table 1.

TABLE 1

|  | Feed wt. % | Distillate wt. % | Residue wt. % |
|---|---|---|---|
| MAH | 1.63 | 1.79 | 1.43 |
| FA | 0.28 | 0.22 | 0.27 |
| PMA | 1.73 | 0.56 | 5.62 |
| PMI | 78.27 | 95.01 | 26.59 |
| PPMA | 1.03 | 0.01 | 3.15 |

TABLE 1-continued

|  | Feed wt. % | Distillate wt. % | Residue wt. % |
|---|---|---|---|
| APSI | 0.45 | 0.01 | 3.25 |
| Others | 16.61 | 2.40 | 59.69 |

As shown in above Table 1, it was confirmed that the contents of PMA, PPMA and APSI having the higher boiling points than the N-phenyl maleimide were remarkably decreased in the distillate of the thin film evaporator. In addition, it was demonstrated that most of the high-boiling-point impurities were removed when the N-substituted maleimide feed was passed through the thin film evaporator in view of the fact that the contents of PPMA and APSI were remarkably increased in the residue of the thin film evaporator. The residue containing the high-boiling-point impurities are discarded, while the amount of PMI contained in the residue may vary depending on the operating conditions of the thin film evaporator, and thus the removal ratio of the high-boiling-point impurities may also vary.

Furthermore, in order to confirm that the impurities having higher boiling points than the N-substituted maleimide were removed in the secondary purification when the lower-boiling-point impurities were removed in the primary purification of Example 3 were removed much more than those in Example 1, the composition of the N-substituted maleimide feed which has passed through the primary purification and was introduced into the thin film evaporator, and the distillate in the thin film evaporator was measured by using liquid chromatography, and the results were shown in below Table 2.

TABLE 2

|  | Feed wt. % | Distillate wt. % |
|---|---|---|
| MAH | 0.87 | 0.71 |
| FA | 0.03 | 0.03 |
| PMA | 0.40 | 0.08 |
| PMI | 88.19 | 98.13 |
| PPMA | 0.47 | 0.00 |
| APSI | 0.30 | 0.00 |
| Others | 9.74 | 1.06 |

As shown in above Table 2, it was confirmed that the contents of PPMA, APSI and Others having higher boiling points than the N-phenyl maleimide were remarkably decreased in the distillate of the thin film evaporator regardless of the amount of the low-boiling-point impurities.

2) Confirming the reduction effect of the polymerization loss ratio (Examples 1 and 2, Comparative Examples 1 and 2)

The N-phenyl maleimide from which the high-boiling-point impurities were completely removed in above Examples 1 and 2 and the N-phenyl maleimide distillate from which the solvent was removed through the primary purification in above Comparative Examples 1 and 2 were put into a flask and boiled at the same temperature of the second distillation column in each of Examples and Comparative Examples in order to indirectly confirm how much polymerization loss occurs at the bottom of the second distillation column in the tertiary purification. Then, samples were taken over time and the purity (%) of the N-phenyl maleimide was measured by using liquid chromatography (LC), and the results were shown in below Table 3 and FIG. 6 (Example 1), FIG. 7 (Example 2), FIG. 8 (Comparative Example 1) and FIG. 9 (Comparative Example 2).

TABLE 3

| Time [min] | 0 | 10 | 20 | 30 | 40 | 50 | 60 |
|---|---|---|---|---|---|---|---|
| Example 1 | 96.2 | 96.9 | 96.0 | 93.0 | 94.7 | 93.9 | 93.0 |
| Example 2 | 98.1 | 93.7 | 92.2 | 89.2 | 90.0 | 90.0 | 84.7 |
| Comparative Example 1 | 76.4 | 75.4 | 73.3 | 70.8 | 69.1 | 69.3 | 66.5 |
| Comparative Example 2 | 75.6 | 71.2 | 63.9 | 59.2 | 54.9 | 53.0 | 46.9 |

The polymerization loss ratio was defined as (the PMI purity of the second distillation column feed—the PMI purity at the bottom of the second distillation column after carrying out the tertiary purification during 1 hour)/(the PMI purity of the second distillation column feed).

Figure 6:
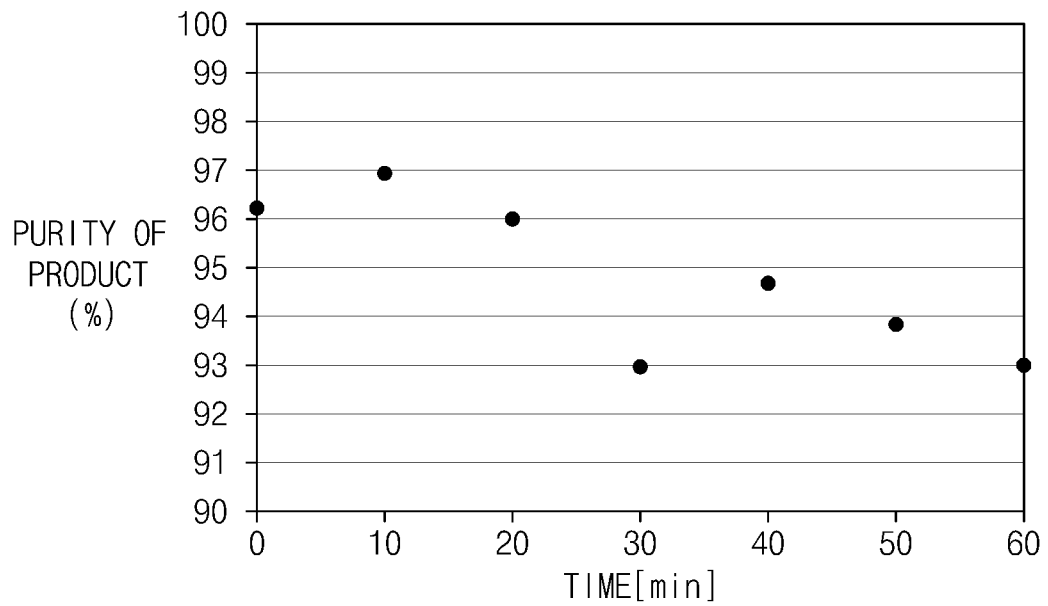
FIG. 6 is a graph showing measured polymerization loss ratio versus temperature and time in Example 1.
Figure 8:
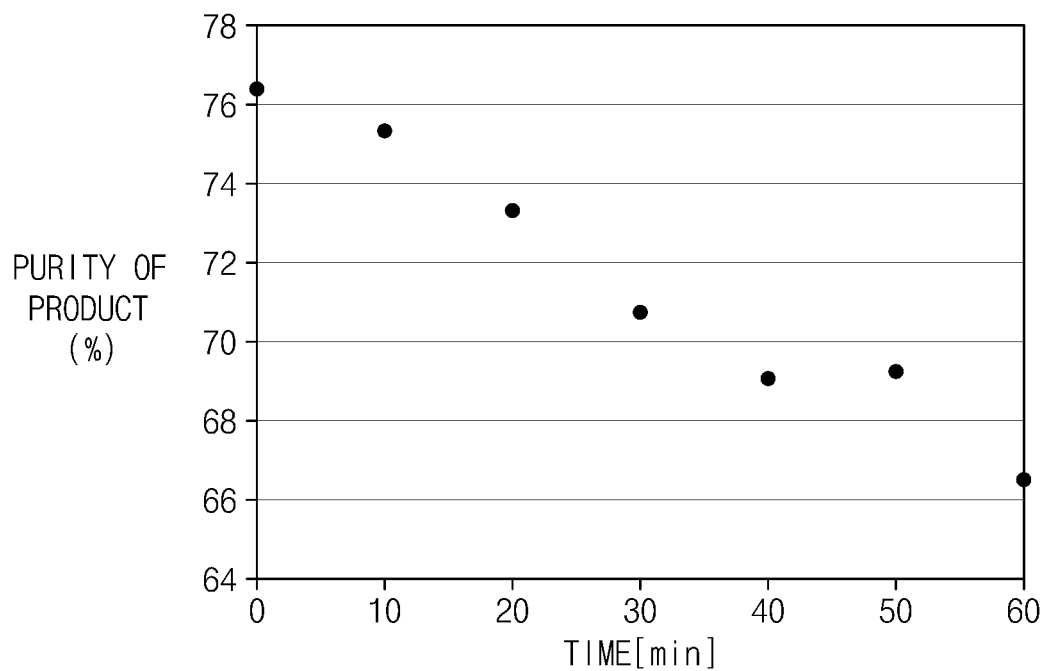
FIG. 8 is a graph showing measured polymerization loss ratio versus temperature and time in Comparative Example 1.

The polymerization loss ratio during 1 hour was 3% at 190° C. in Example 1 as shown in Table 3 and FIG. 6, and the polymerization loss ratio during 1 hour was 13% at 190° C. in Comparative Example 1 as shown in Table 3 and FIG. 8, and thus it was confirmed that the more the high-boiling-point impurities, the greater the polymerization loss.

Figure 7:
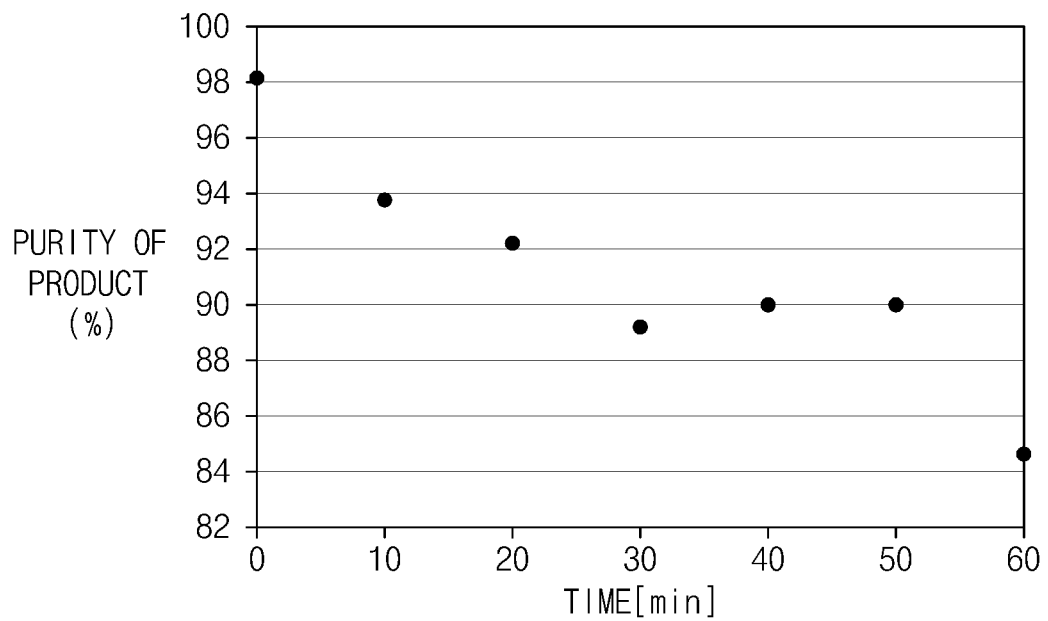
FIG. 7 is a graph showing measured polymerization loss ratio versus temperature and time in Example 2.
Figure 9:
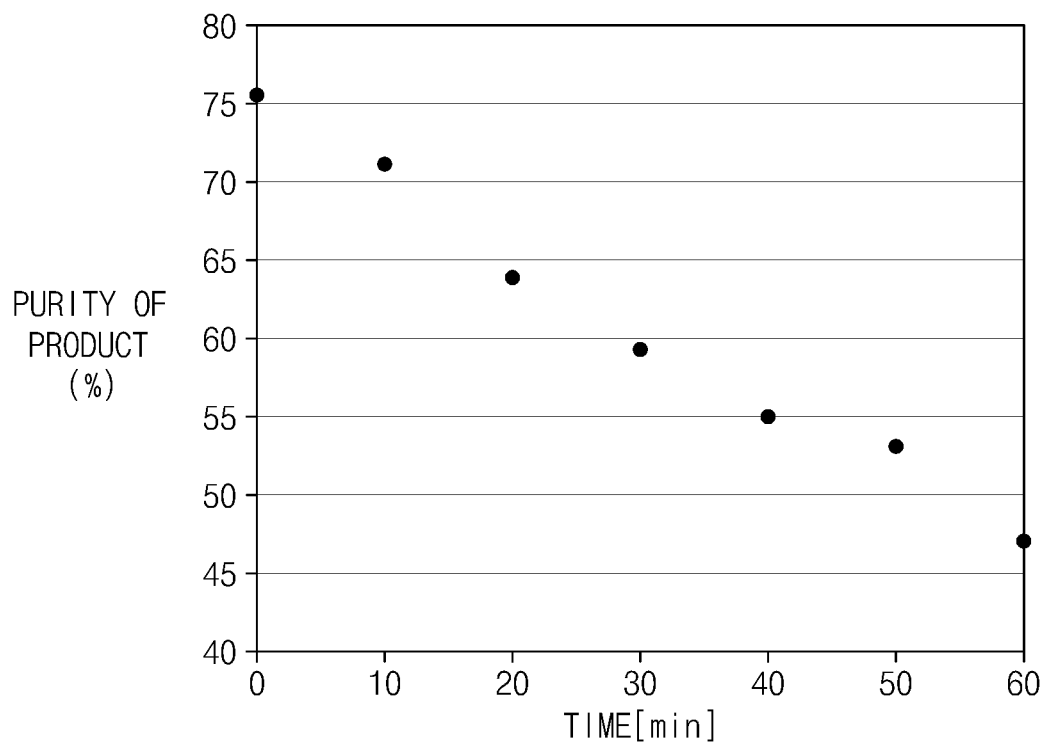
FIG. 9 is a graph showing measured polymerization loss ratio versus temperature and time in Comparative Example 2.

The polymerization loss ratio during 1 hour was 14% at 210° C. in Example 2 as shown in Table 3 and FIG. 7, and the polymerization loss ratio during 1 hour was 38% at 210° C. in Comparative Example 2 as shown in Table 3 and FIG. 9, and thus it was confirmed that the higher the temperature, the greater the effect of the polymerization loss by the high-boiling-point impurities.

Furthermore, when comparing Example 1 with Example 2 or comparing Comparative Example 1 with Comparative Example 2, it was confirmed that the higher the temperature, also the greater the polymerization loss ratio.

Meanwhile, 'Others' mean substances that are not measured in the Liquid chromatography. There are two possibilities for the amounts of 'Others', which is the rest amount excluding the measured amount from the amount filled in for measurement. First, it may be a measurement error, but the error does not exceed more than 5% when a single substance is measured. Another possibility is that a substance having a high molecular weight, for example, the impurities, such as oligomers or polymers of PMI, produced by the polymerization, or the like is not measured in the LC. Therefore, 'Others' may be considered as the high-boiling-point impurities having high molecular weights.

Accordingly, it can be confirmed that when the high-boiling-point impurities were removed previously, the operating temperature of the distillation column can be lowered, but the high-boiling-point impurities having the effects of accelerating the polymerization can be removed, so that the polymerization loss at the high temperature can be minimized according to the above two reasons.

It can be expected that the purification method of the present invention using the evaporation apparatus would minimize the polymerization loss ratio at the bottom of the distillation column through the Experimental Examples.

The above description for the present invention is illustratively provided, and it can be thus understood that a person skilled in the art to which the present invention pertains could easily modify the present invention into another specific form without changing the technical idea or essential features. Therefore, the examples described above are merely illustrative in all the aspects and should be construed as not being limited to the examples set forth herein.

The invention claimed is:

1. A method for purifying N-substituted maleimide, comprising:
   1) performing a primary purification by introducing an N-substituted maleimide solution into a first distillation column and removing an organic solvent by distilling to produce an N-substituted maleimide residue; and
   2) performing a secondary purification by introducing, into an evaporation apparatus, the N-substituted maleimide residue, and removing impurities which have higher boiling points than the N-substituted maleimides.

2. The method for purifying N-substituted maleimide of claim 1, wherein the N-substituted maleimide solution comprises the organic solvent, an unreacted maleic anhydride, an organic acid impurity, and an oligomer in which the N-substituted maleimide is polymerized.

3. The method for purifying N-substituted maleimide of claim 2, wherein the organic acid comprises at least one selected from the group consisting of fumaric acid (FA), maleic acid (MA), maleic anhydride (MAH), N-phenyl maleamic acid (PMA), N-(2,5-dioxo-1-phenyl-3-pyrrolidinyl)-N-phenyl maleamic acid) (PPMA), N-(2,5-dioxo-1-phenyl-3-pyrrolidinyl)-N-phenylfumaramic acid) (PPFA) and 2-anilino-N-phenyl succinimide (APSI).

4. The method for purifying N-substituted maleimide of claim 1, wherein the organic solvent comprises at least one selected from the group consisting of benzene, toluene, xylene, o-xylene, ethylbenzene, isopropylbenzene, cumene, mesitylene, tert-butylbenzene, pseudocumene, trimethylhexane, octane, tetrachloroethane, nonane, chlorobenzene, ethylcyclohexane, m-dichlorobenzene, sec-butylbenzene, p-dichlorobenzene, decane, p-cymene, o-dichlorobenzene, butylbenzene, decahydronaphthalene, tetrahydronaphthalene, dodecane, naphthalene and cyclohexylbenzene.

5. The method for purifying N-substituted maleimide of claim 1, wherein an operating pressure of a first distillation column in the primary purification is from 20 to 80 torr.

6. The method for purifying N-substituted maleimide of claim 1, wherein an operating temperature of a reboiler at the bottom of the first distillation column in the primary purification is from 170 to 220° C.

7. The method for purifying N-substituted maleimide of claim 1, wherein the evaporation apparatus in the secondary purification is at least one selected from the group consisting of a thin film evaporator, a falling film evaporator, and a flash drum.

8. The method for purifying N-substituted maleimide of claim 1, wherein the impurities, which have higher boiling points than the N-substituted maleimide, are at least one selected from the group consisting of N-(2,5-dioxo-1-phenyl-3-pyrrolidinyl)-N-phenyl maleamic acid) (PPMA), N-(2,5-dioxo-1-phenyl-3-pyrrolidinyl)-N-phenylfumaramic acid (PPFA), and 2-anilino-N-phenyl succinimide (APSI).

9. The method for purifying N-substituted maleimide of claim 1, wherein an operating pressure of the evaporation apparatus in the secondary purification is from 5 to 30 torr.

10. The method for purifying N-substituted maleimide of claim 1, wherein an operating pressure of the evaporation apparatus in the secondary purification is from 5 to 10 torr.

11. The method for purifying N-substituted maleimide of claim 1, wherein an operating temperature of the evaporation apparatus in the secondary purification is from 100 to 180° C.

12. The method for purifying N-substituted maleimide of claim 1, wherein the N-substituted maleimide residue in the evaporation apparatus in the secondary purification resides in the apparatus for from 20 seconds to 5 minutes.

13. The method for purifying N-substituted maleimide of claim 1, further comprising, after the second purification:

3) performing a tertiary purification by introducing and distilling, in a second distillation column, the N-substituted maleimide distillate from which the high-boiling-point impurities are removed.

14. The method for purifying N-substituted maleimide of claim 13, wherein an operating pressure of the second distillation column in the tertiary purification is from 20 to 80 torr.

15. The method for purifying N-substituted maleimide of claim 13, wherein a reboiler at the bottom of the second distillation column in the tertiary purification is operated at a temperature from 190 to 230° C.

16. The method for purifying N-substituted maleimide of claim 1, wherein a polymerization loss ratio through the method for purifying N-substituted maleimide is 10% or less at 190° C.

17. The method for purifying N-substituted maleimide of claim 1, wherein the polymerization loss ratio through the purification method for N-substituted maleimide is 30% or less at 210° C.

18. The method for purifying N-substituted maleimide of claim 1, wherein the purity through the method for purifying N-substituted maleimide is 95% or more.

19. The method for purifying N-substituted maleimide of claim 1, wherein the N-substituted maleimide comprises at least one selected from the group consisting of: N-alkyl maleimide such as N-methyl maleimide, N-ethyl maleimide, N-hexyl maleimide, N-octyl maleimide, or N-dodecyl maleimide; N-benzyl maleimide; N-cycloalkyl maleimide such as N-cyclohexyl maleimide; N-phenyl maleimide; and N-substituted phenyl maleimide, in which a phenyl group is substituted with a nitro group, an alkoxy group, an alkyl group, a carboxyl group, a hydroxyl group, or a halogen group, such as N-nitrophenyl maleimide, N-methoxyphenyl maleimide, N-methylphenyl maleimide, N-carboxyphenyl maleimide, N-hydroxyphenyl maleimide, N-chlorophenyl maleimide, N-dimethylphenyl maleimide, N-dichlorophenyl maleimide, N-bromophenyl maleimide, N-dibromophenyl maleimide, N-trichlorophenyl maleimide, or N-tribromophenyl maleimide.

* * * * *